United States Patent
Martinez et al.

(10) Patent No.: US 8,454,630 B2
(45) Date of Patent: Jun. 4, 2013

(54) ENDOSCOPIC CLIPPING DEVICE

(75) Inventors: Michelle D. Martinez, Winston-Salem, NC (US); Brian K. Rucker, King, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 321 days.

(21) Appl. No.: 12/761,692

(22) Filed: Apr. 16, 2010

(65) Prior Publication Data
US 2010/0280533 A1    Nov. 4, 2010

Related U.S. Application Data

(60) Provisional application No. 61/173,872, filed on Apr. 29, 2009.

(51) Int. Cl.
*A61B 17/10* (2006.01)

(52) U.S. Cl.
USPC .......................................... 606/143; 606/158

(58) Field of Classification Search
USPC ......... 606/148, 150, 151, 157, 158, 205–211, 606/213, 215, 216, 219, 221, 142, 143
See application file for complete search history.

(56) References Cited

U.S. PATENT DOCUMENTS

| | | | |
|---|---|---|---|
| 2,594,102 A | 4/1952 | Vollmer | |
| 3,082,426 A | 3/1963 | Miles | |
| 4,296,751 A | 10/1981 | Blake, III | |
| 4,492,232 A | 1/1985 | Green | |
| 5,222,961 A | 6/1993 | Nakao | |
| 5,464,416 A | 11/1995 | Steckel | |
| 6,273,903 B1 | 8/2001 | Wilk | |
| 6,350,269 B1 | 2/2002 | Shipp | |
| 6,527,786 B1 * | 3/2003 | Davis et al. | 606/151 |
| 6,610,073 B1 | 8/2003 | Levinson | |
| 6,679,894 B2 | 1/2004 | Damarati | |
| 6,923,818 B2 | 8/2005 | Muramatsu | |
| 7,081,121 B2 | 7/2006 | Muramatsu | |
| 7,223,271 B2 | 5/2007 | Muramatsu | |
| 7,331,968 B2 | 2/2008 | Arp | |
| 2003/0114851 A1 * | 6/2003 | Truckai et al. | 606/51 |
| 2005/0049618 A1 | 3/2005 | Masuda | |
| 2005/0125010 A1 * | 6/2005 | Smith et al. | 606/142 |
| 2007/0282355 A1 | 12/2007 | Brown | |
| 2008/0103510 A1 | 5/2008 | Taylor | |

OTHER PUBLICATIONS

Boston Scientific Resolution Clip—internet printout—printed Oct. 23, 2008 (3 pages).
Olympus EndoTherapy—internet printout—printed Apr. 2, 2010—various Olympus Clipping devices.
Search Report and Written Opinion dated Jul. 26, 2010 for related PCT/US2010/031845.

* cited by examiner

*Primary Examiner* — Thomas McEvoy
(74) *Attorney, Agent, or Firm* — Brinks Hofer Gilson & Lione (57) ABSTRACT

A hemostatic clipping device is provided. The device includes first and second elongate arms, each arm comprising distal and proximal end portions, the arms being connected to allow relative motion between the first and second arms, the distal portion of each of the first and second arms further comprising a track blindly defined from a distal end of each arm toward the proximal portion of each arm. A clip is slidably disposed between the opposed distal portions of each of the first and second arms, the clip comprising first and second fingers each with distal and proximal portions, the proximal portions of the first and second fingers being fixed together to bias the distal portions of the first and second fingers toward each other, the first and second fingers each further comprising a pin extending radially outward from the distal end portion thereof.

27 Claims, 6 Drawing Sheets

ENDOSCOPIC CLIPPING DEVICE

CROSS-REFERENCE TO RELATED APPLICATIONS

This application claims priority under 35 U.S.C. 119(e) of U.S. Provisional Application No. 61/173,872, filed on Apr. 29, 2009, the entirety of which is hereby fully incorporated by reference herein.

TECHNICAL FIELD

The present disclosure relates to a clip, and more specifically to a clip that can be used to cause homeostasis of blood vessels along the gastrointestinal tract, and a device for application of clips to the gastrointestinal tract.

Conventionally, a clip may be introduced into a body cavity through an endoscope to grasp living tissue of a body cavity for hemostasis, marking, and/or ligating. In addition, clips are now being used in a number of applications related to gastrointestinal bleeding such as peptic ulcers, Mallory-Weiss tears, Dieulafoy's lesions, angiomas, post-papillotomy bleeding, and small varices with active bleeding.

Gastrointestinal bleeding is a somewhat common and serious condition that is often fatal if left untreated. This problem has prompted the development of a number of endoscopic therapeutic approaches to achieve hemostasis such as the injection of sclerosing agents and contact thermo-coagulation techniques. Although such approaches are often effective, bleeding continues for many patients and corrective surgery therefore becomes necessary. Because surgery is an invasive technique that is associated with a high morbidity rate and many other undesirable side effects, there exists a need for highly effective, less invasive procedures.

Mechanical hemostatic devices have been used in various parts of the body, including gastrointestinal applications. Such devices are typically in the form of clamps, clips, staples, sutures, etc. that are able to apply sufficient constrictive forces to blood vessels so as to limit or interrupt blood flow. One of the problems associated with conventional hemostatic devices, however, is that they can only be delivered using rigid shafted instruments via incision or trocar cannula. Moreover, many of the conventional hemostatic devices are not strong enough to cause permanent hemostasis.

Another problem often encountered with conventional hemostatic devices is the difficulty in securing the clip device to the delivery apparatus prior to reaching the target area within the patient, and then quickly and easily releasing the clip device from the delivery apparatus once the clip has been attached to the target site.

BRIEF SUMMARY

A first representative embodiment of a clipping device is provided. The device includes first and second elongate arms, each arm comprising distal and proximal end portions. The arms are connected to allow relative motion between the first and second arms. The distal portion of each of the first and second arms include a track blindly defined from a distal end of each arm toward the proximal portion of each arm. A clip is slidably disposed between the opposed distal portions of each of the first and second arms, the clip comprising first and second fingers each with distal and proximal portions. The proximal portions of the first and second fingers are fixed together to bias the distal portions of the first and second fingers toward each other. The first and second fingers each include a pin extending radially outward from the distal end portion thereof. The pin from the first finger is slidably received within the track of the first arm, and the pin from the second finger is slidably received within the track of the second arm.

A second representative embodiment of a clipping device is provided. The device includes first and second elongate arms, each arm comprises distal and proximal end portions. The arms are pivotably connected to allow selective pivoting between a first closed position where the first and second arms are disposed substantially parallel to each other and a second open position where the first and second arms are disposed at oblique angles with respect to each other. The distal portion of each of the first and second arms further comprising a track blindly defined from a distal end of each arm toward the proximal portion of each arm. A clip is slidably disposed between the opposed distal portions of each of the first and second arms, and includes first and second fingers each with distal and proximal portions, the first and second fingers each further comprise a pin extending radially outward from the distal end portion thereof. The pin from the first finger is slidably received within the track of the first arm, and the pin from the second finger is slidably received within the track of the second arm. The proximal portions of the first and second fingers being fixed together to bias the distal portions of the first and second fingers toward each other such that the first and second arms are biased to the closed position when the pins from the respective fingers are engaged with the tracks on the respective arms.

Another representative embodiment of a clipping device includes an elongate flexible cannula with two pivotable arms attached thereto. The arms are remotely pivotable with one or more transmission members engaged thereon. The arms each include slots defined blindly through the distal portion thereof, which receive outwardly extending pins from opposed fingers of a clip. The clip is biased inward such that the arms when force is applied thereto and closed when the force is removed due to the inward biasing force of the clip.

Still another representative embodiment of a clipping device includes a flexible clip with first and second opposed fingers, each finger includes a jaw portion disposed on the distal end thereof and a pin radially extending outward from an outer surface of the clip. The first and second fingers are mated together and configured to be biased into a closed position with the first and second jaws in close proximity to each other.

Another representative embodiment of the disclosure includes a clip with an elongate first finger and an elongate second finger, each of the first and second fingers comprise proximal ends mated to each other to urge opposed distal ends of each finger toward each other. A pin radially extends outward from an outer surface of the respective finger proximate the distal end of the respective finger. Jaws are defined upon the distal end of the first and second fingers that each extend toward the jaw on the opposite of the first and second fingers.

Advantages of the present disclosure will become more apparent to those skilled in the art from the following description of the preferred embodiments of the disclosure that have been shown and described by way of illustration. As will be realized, the disclosed subject matter is capable of other and different embodiments, and its details are capable of modification in various respects. Accordingly, the drawings and description are to be regarded as illustrative in nature and not as restrictive.

DETAILED DESCRIPTION OF THE DRAWINGS AND THE PREFERRED EMBODIMENTS

Turning now to FIGS. 1-4, a first representative embodiment of a hemostasis clip applicator device 10 is provided. The device includes a pair of first and second arms 20, 30 that are pinned together and pivot with respect to each other with a scissor-like mechanism. The first and second arms 20, 30 receive one or more hemostasis clips 70 therebetween, which may be expelled from the device 10 to mechanically close an open wound in a patient's GI tract or in another similar area of the patient, such as a human or a mammal. A cannula 60 extends rearwardly from the first and second arms 20, 30 and may extend remotely from the arms to define the proximal end of the device 10. The cannula 60 receives a stylet or rod 66 therethrough, which may be moved within the cannula 60, to urge the distal most clip 70 out of the device 10 when the clip 70 is applied to the patient's tissue, and advance the next clip within the device 10 to a position proximate the distal ends 22, 32 of the first and second arms 20, 30. In some embodiments, the stylet 66 may include markings upon the proximal end portion thereof (i.e. the portion that extends out of the cannula 60) that are spaced at substantially the same distance apart as the length of the clips 70 (or with another suitable arrangement), to provide the user with a visual reference guide for precise application of one clip onto the patient at a time, and properly positioning the next clip 70 for application onto the patient. In some embodiments, the cannula 60 may be formed by a tightly coiled coilspring, which defines a lumen therein. The cannula 60 may be about 230 cm to provide sufficient length for placement into the desired locations within the GI tract that are conventionally reachable endoscopicly. The cannula 60 may include an outer low friction coating thereon, such as PET, PEBAX, TEFLON®, PEEK, Nylon, or the like to minimize friction associated with insertion of the device 10 into the patient.

The first arm 20 is an elongate member that includes a distal end portion 22 and a proximal end portion 24 with a pinned connection therebetween. The first arm 20 is pivotally connected to a second arm 30 with a pinned or similar connection 40 that aligns and allows relative pivoting of the two arms 20, 30 with respect to each other. The pinned connection 40 may be with a single pin that extends through apertures in both the first and second arms 20, 30 (and the cannula 60). In other embodiments, the pinned connection may be formed with two pins that are substantially collinear with each other and independently connected to opposite sides of the cannula 60. The use of two pins allows for the pivotable pinned connection 40 between the first and second arms 20, 30 (i.e. each arm is pinned to the stationary cannula 60) while maintaining the lumen within the cannula 60 open for passage of the stylet 66 therethrough.

The second arm 30 is constructed similarly to the first arm 20 and similarly includes a distal end portion 32 and a proximal end portion 34 with the pinned connection 40 therebetween. The outer geometry of each of the first and second arms 20, 30, are substantially semi-circular such that the outer surface of the first and second arms 20, 30 forms a substantially circular cross-section along the length the device 10 when the first and second arms 20, 30 are aligned in the closed position (FIGS. 1, 3), as discussed below. In some embodiments, the device 10 is configured to fit within and be translated along a 2.8 mm endoscope channel. In other embodiments, the device is configured to travel within differing sized lumens, such as 3.2 mm and other commonly used endoscope channels. Alternatively, the device 10 may be sized and configured to be inserted through the lumens of flexible sheaths or catheters in addition to or instead of an endoscope.

The distal end portion 22, 32 of each of the first and second arms 20, includes a track 28 defined blindly along the length of the distal end portion 22, 32 from the distal end thereof through at least a portion of the length of the distal end portion 22, 32 of the respective arm 20, 30. The track 28 is of a length sufficient to receive pins 78 extending from the number of clips 70 intended to be disposed within the device 10. Specifically, as discussed in detail below, one, two, or more clips 70 may be disposed between the distal portions 22, 32 of the first and second arms 20, 30 with pins 78 extending from the clips 70 being slidably received within the track 28 in the respective arm. For example, for devices intended to carry two clips 70, the track 28 must be at least slightly longer than the length of a first clip 70, and a portion distal end of the second (rearwardly installed) clip 70 between the distal tip and the outwardly extending pin 78, such that the pins 78 from each clip 70 disposed between the arms 20, 30 are slidably received within the track. In other embodiments where the device is configured to retain three or more clips 70, the track 28 must be at least slightly longer than two clips (i.e. the track 28 must be slightly longer than the combined length of one clip less than the number of clips 70 to be positioned within the device 10).

Figure 13:
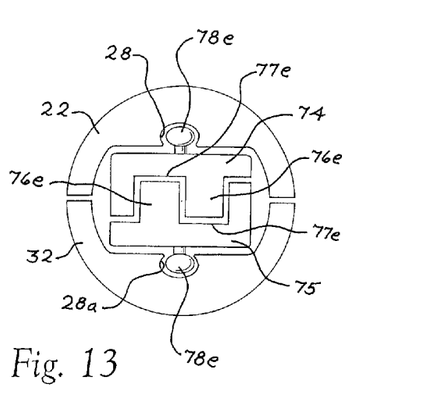
Figure 14:
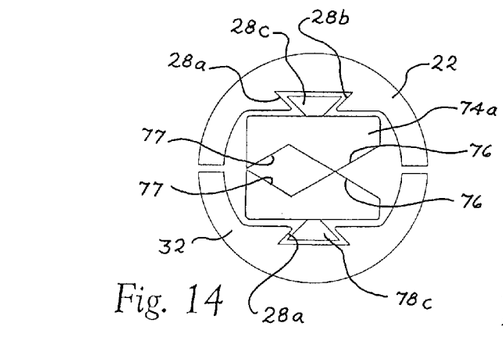
Figure 15:
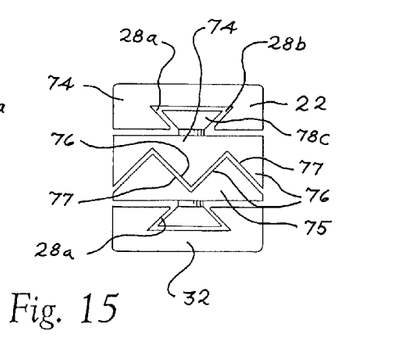

The track 28 may be a slit that is defined through the entire wall thickness of the arm (FIG. 10) or an alternate track 28 may be defined through only a portion of the wall thickness of the arm (FIG. 13) to provided for arms 20, with added strength. The track 28 may include parallel side walls, curved side walls, or may define a keyway 28a (FIGS. 11, 14, 15).

The proximal end portion 24, 34 of each of the first and second arms 20, 30, and the pinned connection 40 of each arm, surrounds a cannula, or tube 60 that extends rearwardly beyond the first and second arms 20, 30. The cannula 60 is an elongate member that provides a lumen for communication with and operation of the arms 20, 30 to allow the device 10 to be remotely operated when inserted through and out of the endoscope within a patient. The cannula 60 provides a lumen for travel of an elongate stylet that extends through the cannula 60 and selectively engages the proximal end portion 71 of the rearmost clip 70 disposed between the first and second arms 20, 30. The stylet 66 may be urged further into the cannula 60, which subsequently urges the distal most clip 70 out of the device 10, to allow that clip 70 to remain within the patient and maintain the patient's tissue closed between the jaws 74, 75 of the clip 70, discussed below.

Figures 1, 2:
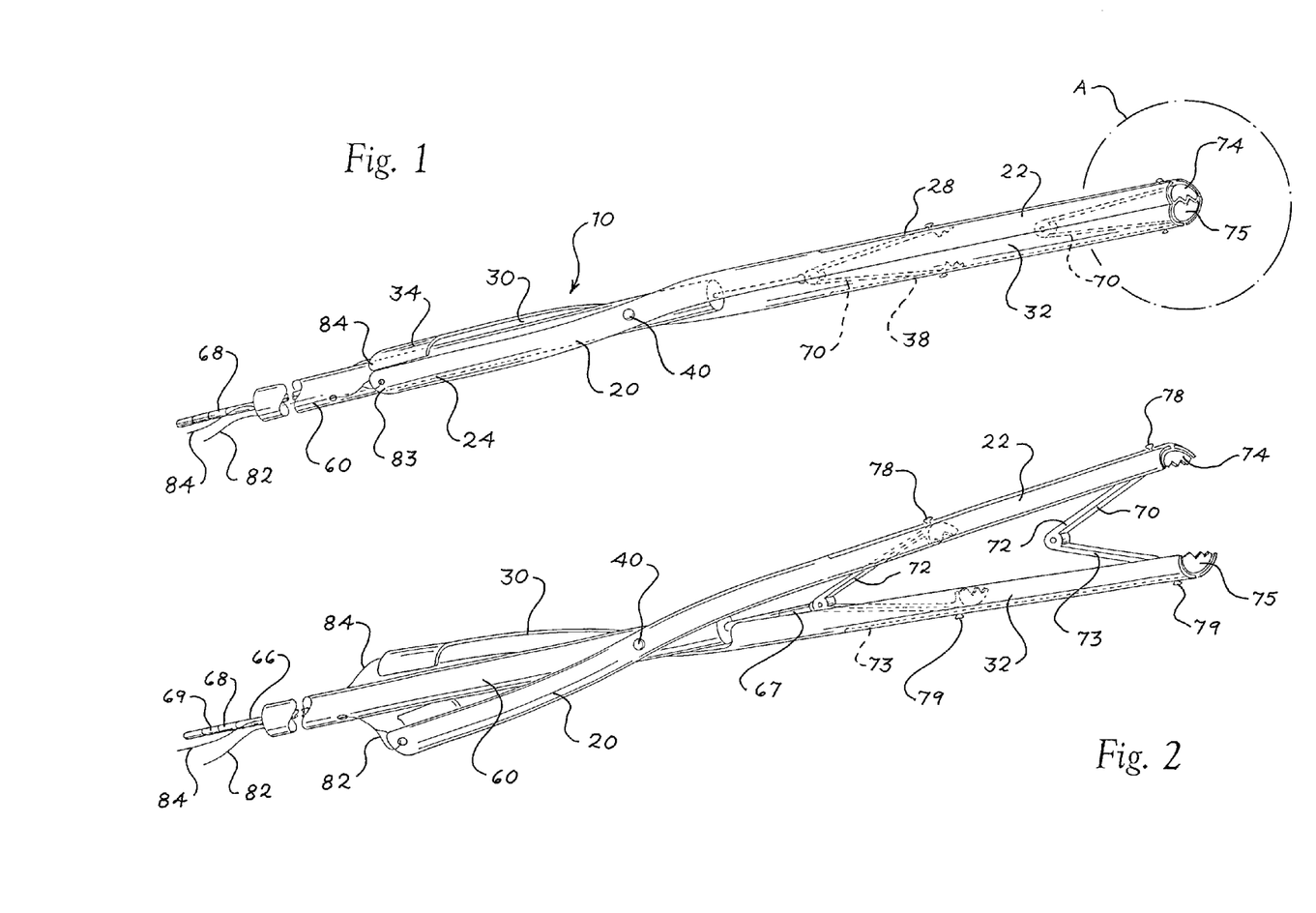
FIG. 1 is a perspective view of a first hemostatic clipping device in the closed position with two clips disposed therein.
FIG. 2 is the clipping device of FIG. 1 in the open position.
Figures 3, 4:
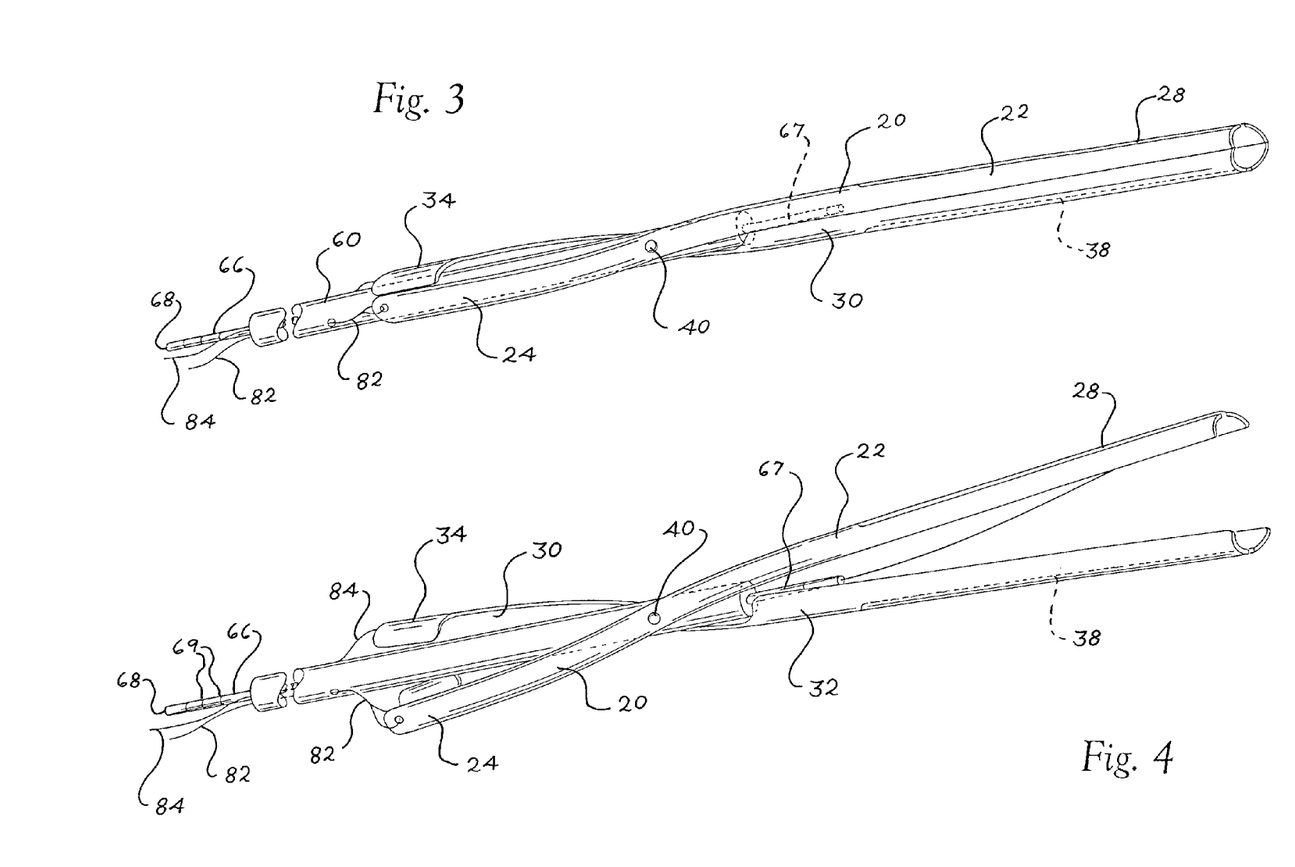
FIG. 3 is a perspective view of the clipping device of FIG. 1 in the closed position.
FIG. 4 is the view of FIG. 3 with the clipping device in the open position.

The cannula 60 also may support and enclose two or more operational wires 82, 84 that extend from the first and second arms 20, 30 and may be manipulated by the physician to remotely transfer the device 10 from the first closed position (FIG. 1) to the second, open position (FIG. 2). In some embodiments, the wires 82, 84 are enclosed within the cannula 60 and extend out of the cannula 60 at the proximal end 64 thereof. The cannula 60 and wires 82, 84 may be engaged with a handle 90 and an operator 92 in an arrangement to cause the wires to be selectively pulled in tension by the operator 92 to create a tensile force within the wires and accordingly pull the proximal ends of the first and second arms 20, 30 away from each other (and accordingly the distal ends 22, 32 of the arms to similarly pivot away from each other) by virtue of the scissors-like pinned connection 40.

Figures 5, 6:
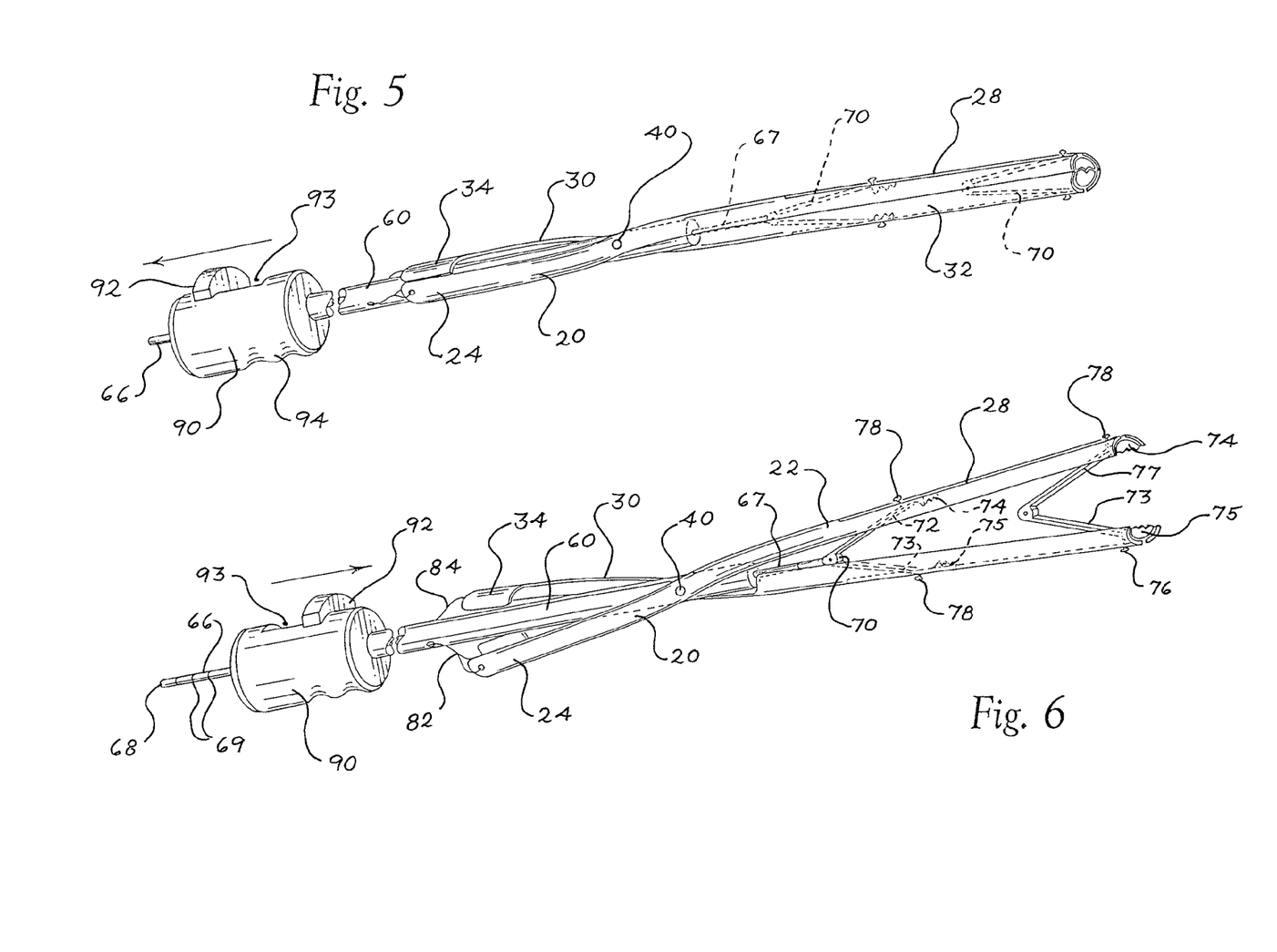
FIG. 5 is a perspective view of a hemostatic clipping device in the closed position.
FIG. 6 is the device of FIG. 5 in the open position.

In other embodiments, the wires 82, 84 may be pressed in compression within the cannula 60 by the operator 92 that is slid forwardly within a track 93, which causes the proximal ends 24, 34 of the arms 20, 30 (and therefore the distal ends 22, 32 of the arms on the opposite side of the pivot point 40) to extend away from each other against the inward biasing force of the clips 70. Due to the continuous inward biasing force of the clips 70, the user must hold the operator 92 in the active position (e.g. the forward position within track 93 as shown in FIG. 6) to maintain the clip 70 and arms 20, 30 open during the hemostasis clipping procedure.

In some embodiments, the first and second wires 82, 84 are connected to separate and dedicated operators 92 such that the first and second arms 20, 30 (and therefore the respective finger 72, 73 connected to the respective arm) can be independently pivoted while the other of the first and second arm 20, 30 remains stationary. The dedicated operator may be similar to operator 92, with the two dedicated operators disposed on opposite sides of the handle 90, proximate to each other such that the user's thumb or finger engaging the operator can comfortably manipulate both operators simultaneously, or a single operator at a time.

The wires 82, 84 may be connected to the proximal ends of the arms 20, 30 by forming a loop (see FIG. 1) that extends through an aperture in the respective arm, or using other known structures to fix the arms 20, 30 within the wires. The wires 82, 84 may be made from thinly drawn stainless steel, Nitinol, or another metal strong enough to carry the required compressive (or tensile force) but not contribute significantly to the overall size, weight, and cost of the device. In some embodiments, the wires 82, 84 are made from a material that is stiff enough to avoid buckling or bending when the wires are pushed to rotate the arms 20, 30 away from each other. In some embodiments, the cannula 60 defines one or more wire lumens that support and direct the wires from the handle 90 to the arms 20, 30 and includes an inner cross-section similar to the outer cross-section of the wires to prevent the wires from buckling or bending therewithin when placed under a compressive load. The arms 20, 30 are configured to rotate toward each other when force placed thereon by the wires 82, 84 (ultimately from the operator 92) is released. The clips 70 slidably disposed between the distal end portions 23, 32 of the first and second arms 20, 30 are biased toward a closed position (FIGS. 1, 7, and 9), and the closing biasing force of the clips 70 urge the arms toward each other when the force thereon from the wires (and operator 92) is released.

In other embodiments, the first and second arms 20, 30 may be remotely rotated with force transmission mechanisms other than elongate wires 82, 84. For example, in some embodiments, the distal end portion 67 of the stylet 66 (or cannula 60 if relative motion is possible between the cannula 60 and the arms 20, 30) may have a plurality of gear teeth (such as rack teeth) that engage complimentary teeth (such as pinion teeth) disposed upon the first and second arms 20, 30 such that longitudinal motion of the stylet 66 (or cannula 60) causes rotation of the arms 20, 30. Other known force transmission structures are contemplated to allow for remote pivoting of the arms 20, 30.

Figure 7:
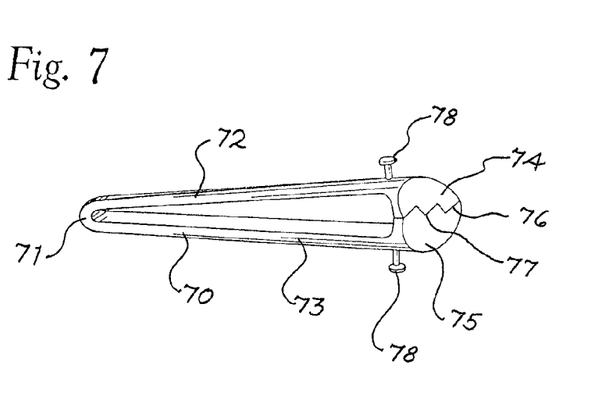
FIG. 7 is a side view of clip usable with the device of FIG. 1 in the closed position.
Figure 8:
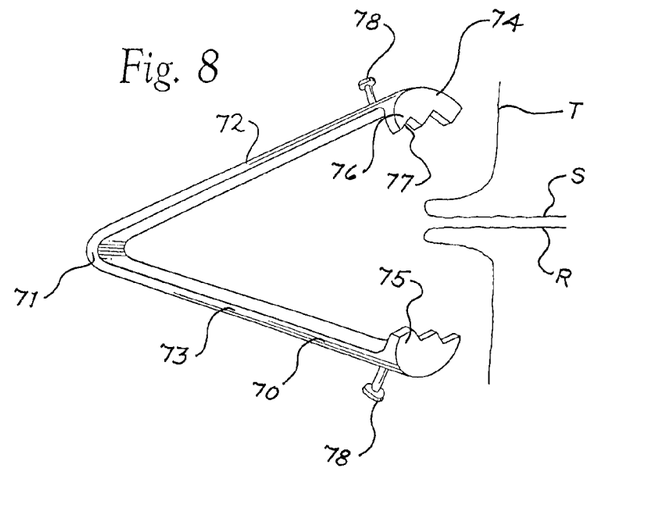
FIG. 8 is the clip of FIG. 7 in the open position shown schematically proximate to tissue to be closed with the clip.
Figure 9:
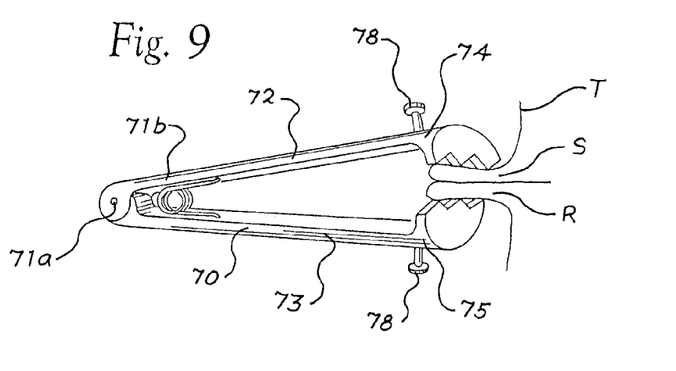
FIG. 9 is the view of FIG. 8 with the clip in the closed position and closing the tissue.

One or more clips 70 may be provided between the distal end portions of the first and second arms 20, 30 with the clips 70 arranged in a series relationship such that the proximal end of the outer-most clip 70 (i.e. the clip 70 that is first released from the arms 20, 30 with distal movement of the stylet 66 (discussed below)) is disposed proximate or contacting the distal end of the next clip 70 disposed within the device 10. As shown in FIGS. 7-9, the clips 70 include first and second fingers 72, 73 that are fixed or connected together at the proximal ends 71 thereof. In some embodiments, the first and second fingers 72, 73 may be monolithically formed together with the two fingers 72, 73 worked, bent, or otherwise transferred to the final shape of the clip 70. In other embodiments, the first and second fingers 72, 73 may be two separate members attached together with a joint at a proximal end, such as a pinned joint, a weld joint, with adhesive, mechanical fasteners, and the like.

The first and second fingers 72, 73 may be biased toward each other, i.e. the first and second fingers 72, 73 are biased together such that the distal portions thereof, and specifically the jaws 74, 75 of the respective first and second fingers 72, 73 are biased to normally engage each other (or maintain close proximity with each other). In some embodiments, the inward biasing force of the first and second fingers 72, 73 of the clips 70 are biased together with a biasing force established as the material forming the first and second fingers 72, 73 is worked into the orientation where the first and second fingers 72, 73 are aligned substantially parallel with each other. The first and second fingers 72, 73 may be configured to be biased together to provide a compressive force between the first and second jaws 74, 75 when the jaws engage, which assists in tightly holding tissue therebetween. In embodiments where the first and second fingers 72, 73 are pinned or otherwise fixed together, the first and second fingers 72, 73 may be biased together with a spring (such as a helical spring). 71b (FIG. 9) disposed in concert with the proximal end connection therebetween. The first and second fingers 72, 73 are configured to be expandable to an open configuration (FIGS. 2, 8) with the pivoting of the first and second arms 20, 30 (due to engagement between the pins 78 and the track 28 to allow the jaws 74, 75 to disengage to be aligned with the patient's tissue (T, S, R, FIGS. 8-9) to be closed via the clip 70. As discussed in detail below, when the jaws of the clip 70 are properly aligned with the desired tissue T, S, R to be closed, the outward force upon the first and second fingers 72, 73 is released (by allowing the arms 20, 30 to return to the closed position when the operator 92 is released) and the clip 70 returns to the normal closed position, with the jaws 74, 75 of the clip 70 engaging the desired tissue T, S, R (FIG. 9).

As shown in FIGS. 10-15, the jaws 74, 75 of the respective first and second fingers 72, 73 may be configured with several patterns or shapes, and may be configured such that the first and second jaws 74, 75 engage when the clip 70 is in the normal engaged position (FIGS. 1, 7, 9). For the sake of understanding, FIGS. 10-15 depict the jaws 74, 75 in close proximity in the closed position. One of skill in the art will understand that the jaws 74, 75 depicted in FIGS. 10-15 may be configured to normally contact each other when in the closed position.

Figure 10:
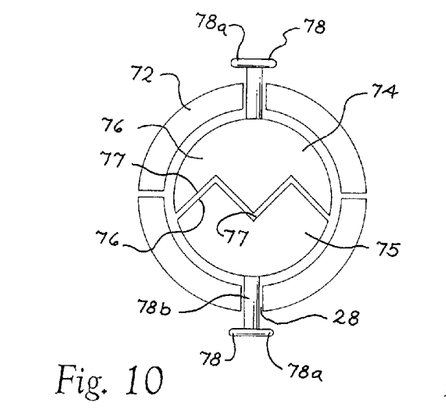
FIGS. 10-15 are front views of detail A of FIG. 1 showing various configurations of the distal end of the first and second arms and the distal end of the first and second fingers.
Figure 11:
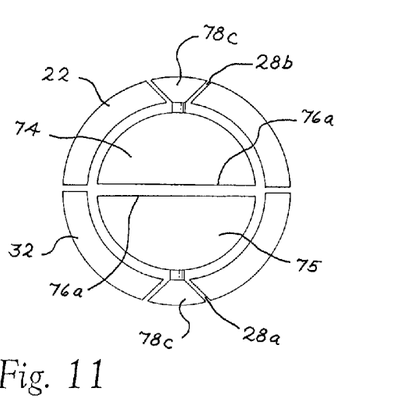
Figure 12:
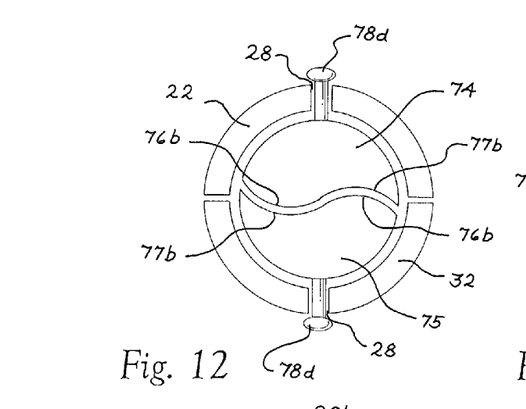

As shown in FIG. 10, the first and second jaws 74, 75 may include a one or more ridges 76 and valleys 77 disposed thereon, which form teeth upon the jaws. The ridges 76 and valleys 77 may be substantially the same size and shape as the ridges 76 and valleys 77 disposed upon the opposite jaw and may be disposed in opposite locations upon the opposite jaws, such that the ridges 76 on a first jaw 74 are aligned in registry with the valleys 77 on the second jaw 75, and the ridges 76 on the second jaw 75 are aligned in registry with the valleys 77 on the first jaw 74 when the clip 70 is in the normal position. In other embodiments shown in FIG. 14, the ridges 76 and valleys 77 on opposite jaws 74, 75 may be disposed in registry with each other, such that the tips of the 74 contact each other (or are aligned in close proximity to each other), when the clip 70 is in the normal position.

In still other embodiments, the jaws 74, 75 may have a plurality of different shapes, such as flat surfaces (FIG. 11), oppositely stepped surfaces 76e, 77e either in registry (FIG. 13) or out of registry, or arcuate surfaces 76b, 77b either in registry (FIG. 12) or out of registry. In some embodiments, the first and second jaws 74, 75 may have two or more ridges 76 and valleys 77 thereon that may be in registry (i.e. the ridges 76 on one jaw align with the valleys 77 on the opposite jaw, shown in FIG. 15) or not in registry.

As discussed above and shown in FIGS. 10-15, each of the first and second fingers 72, 73 includes a pin 78 that extends radially outward from the outer surface of each pin. In some embodiments, the pin 78 is disposed proximate the distal end of the respective finger 72, 73, and proximate to the jaw 74, 75 on each finger. The pin 78 is configured to be received within the track 28 defined within the distal end portion 22, 32 of the respective first and second arm 20, 30. In some embodiments, the pin 78 may be a cylindrical member with an enlarged head portion 78a (FIG. 10), with cylindrical body portion configured to extend between the walls of the respective arm that defines the track 28 and the head portion disposed in contact with outer surface of the arm, to retain the pin 78 engaged with the track 28 against the inward biasing force of the clip 70. In some embodiments, the head portion may be cubic or boxlike (FIG. 10), spherical (FIG. 12, 78d), disc-shaped, elliptical, or formed in any shape with a diameter large enough to retain the pin 78 within the track 28 against the biasing force of the clip 70.

In other embodiments shown in FIGS. 11, 14, and 15, the pin 78 may be (or include) a key 78c where the sides thereof are nonparallel and are configured to ride within a similarly sized keyway 28b defining the track 28a within the respective arm. In some embodiments shown in FIGS. 13-15, the track 28 is defined only partially through the wall of the arm, the pin 78 is sized with a head configured to slide within an open volume within the track 78 to maintain the sliding connection between the two against the inward biasing force of the clip 70. In some embodiments shown in FIG. 15, the distal end portions 22, 32 of the first and second arms 20, 30 (and potentially the entire length of the first and second arms 20, 30) are formed with a width substantially equal to the width of the first and second fingers 72, 73 (and jaws 74, 75) of the clip 70 to minimize the overall width and size of the device 10 that is inserted through the lumen of the endoscope and into the patient for use.

In some embodiments, the clip 70 may be formed from Nitinol or various alloys thereof to take advantage of the superelastic properties of Nitinol. In some embodiments, the clip 70 may be formed from alloys of Nitinol that exhibit radiopaque properties, such as alloys with about 3 to about 14 percent palladium, or other radiopaque elements. The clips 70 may be formed in various shapes and sizes, but generally the opposed fingers 72, 73 are substantially parallel when the fingers are in the relaxed position (FIGS. 7, 9). The clips 70 may be approximately 0.5 inches long with the first and second fingers 72, 73 configured to be expandable to form an opening of about 11 mm between the opposed jaws 74, 75 when in the open position (FIG. 8). As understood, the clips 78 (and other portions of the device 10) may be constructed in different shapes and sizes for other uses within the patient. The clips 70 are configured to be strong enough to be openable and closable a plurality of times during operation of the device 10, while maintaining the biasing force to the closed position after multiple cycles of the clip 70.

Figures 16, 17:
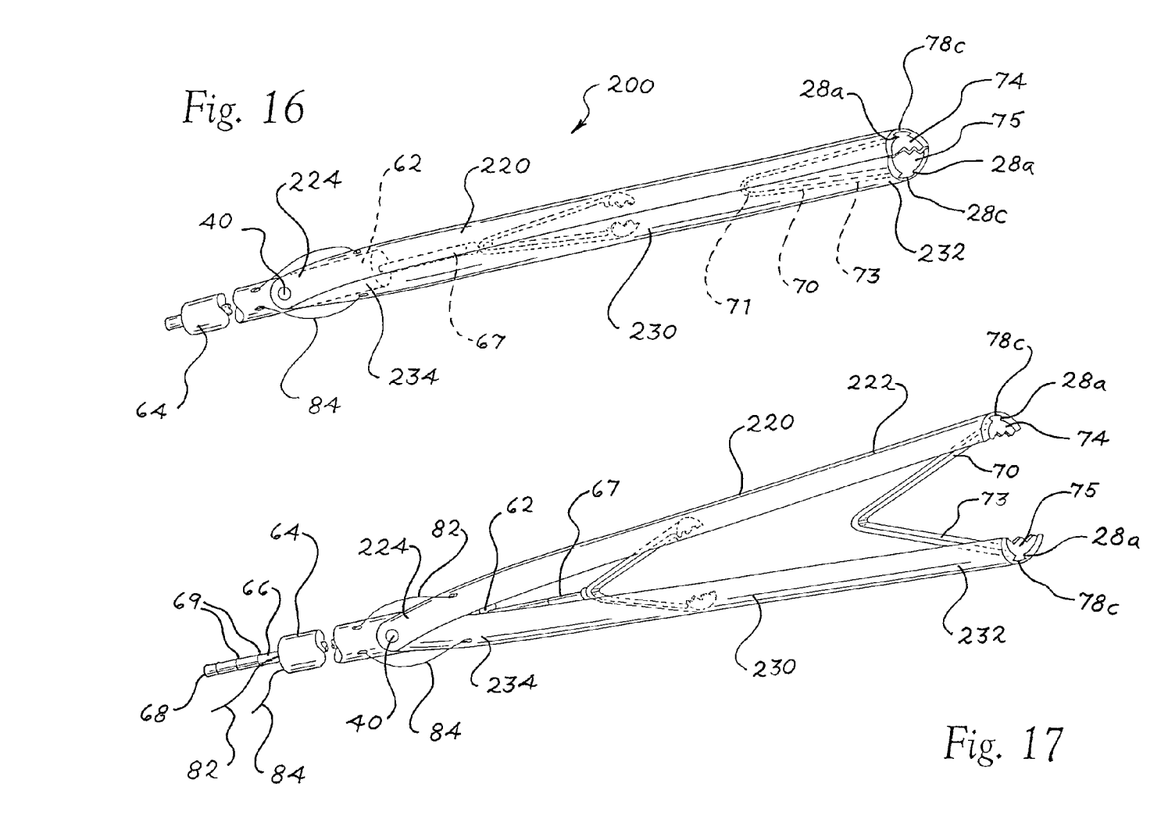
FIG. 16 is a perspective view of another hemostatic clipping device in the closed position.
FIG. 17 is the clipping device of FIG. 16 in the open position.

Turning now to FIGS. 16-17, another representative embodiment of a hemostatic clipping device 200 is provided. The device 200 includes many of the same components as discussed with respect to the device 10, above, and for the sake of brevity similar components are discussed with like element numbers. The device 200 includes first and second arms 220, 230 that are pivotably attached at pivot point 40, a cannula 60 that extends between a proximal portion of the first and second arms 220, 230 and further extends proximally of the arms for a large distance, such as 230 cm. The cannula 60 is configured to receive a stylet or rod 66 therethrough to aid in the positioning and removal of clips 70 disposed between the first and second arms 220, 230.

The first arm 220 is an elongate member that includes a distal end portion 222 and a proximal end portion 224. The first arm 220 is pivotally connected to a second arm 230 with a pinned or similar connection 40 that aligns and allows relative pivoting of the two arms 220, 230 with respect to each other. The first and second arms 220, 230 are pivotably connected together with the pivot point 40 disposed proximate the proximal end of each arm 220, 230, such that the arms form a "V" shape when the arms are pivoted to the open position (FIG. 17). The pinned connection 40 may be with a single pin that extends through apertures in both the first and second arms 220, 230 (and the cannula 60). In other embodiments, the pinned connection 40 may be formed with two pins that are substantially collinear with each other and independently connected to opposite sides of the cannula 60. The use of two pins allows for the pivotable connection between the first and second arms 220, 230 (i.e. each arm is pinned to the stationary cannula 60) while maintaining the lumen within the cannula 60 open for passage of the stylet 66 therethrough.

The second arm 230 is constructed similar to the first arm 220 and similarly includes a distal end portion 232 and a proximal end portion 234. The outer geometry of each of the first and second arms 220, 230 may be substantially semi-circular such that outer surface of the first and second arms 220, 230 collectively forms a substantially circular cross-section along the length the device 200 when the first and second arms 220, 230 are aligned in the closed position (FIG. 16), as discussed below. In some embodiments, the device 200 is configured to fit within and be translated along a 2.8 mm endoscope channel. In other embodiments, the device is configured to travel within differing sized lumens, such as 3.2 mm and other commonly used endoscope channels. Alternatively, the device 200 may be sized and configured to be inserted through flexible sheaths or catheters rather than or in addition to an endoscope The distal end portion of each of the first and second arms 220, 230 include a track 28 (shown as an internal keyway 28a in FIGS. 16-17, but may be similar to other tracks 28 discussed above and depicted in FIGS. 10-15). The track 28 that is defined blindly along the length of the respective arm 220, 230 from the distal end thereof and is of a length sufficient to receive pins 78 extending from the number of clips 70 that are intended to be disposed within the device 10. As with the device 10, the tracks 28 are configured to receive one, two, or more clips 70 between the first and second arms 220, 230. The track 28 is configured to receive clips 70 with the various size and shape pins 78 and jaws 74, 75 that are discussed in the embodiments above.

The first and second arms 220, 230 are remotely openable with an operator (see FIGS. 5, 6, elements 92, 93) that is movably connected to a handle 90 (FIGS. 5-6), which is provided at the proximal end of the cannula 60 such that the operator 92 is manipulable when the device 200 is inserted within the patient (and the endoscope) and disposed proximate tissue to be closed with the clips 70. Similar to the device 10, the operator 92 selectively pivots the first and second arms 220, 230 away from each other with the aid of wires 82, 84 (or other force transmission mechanisms discussed above) that are disposed therebetween. The wires 82, 84 may connect with the first and second arms 220, 230 forward of the pivot point 40 therebetween, such that pulling the wires in tension (due to movement of the operator 92 with respect to the handle 90) causes the first and second arms 220, 230 to pivot away from each other, and therefore open the fingers 72, 73 (and jaws) of the clip 70 (FIG. 17). In other embodiments, the wires and the first and second arms 220, 230 may be configured such that pushing the wires in compression may urge outward pivoting of the arms 220, 230. Because the fingers of the one or more clips 70 connected to the first and second arms 220, 230 are biased toward the closed position, the clips 70 urge the first and second arms 220, 230 to pivot toward each other when the force in the wires is released. The wires 82, 84 may be threaded through a lumen of the cannula 60 between the proximal ends of the first and second arms 220, 230 and the operator 92, and in some embodiments, the cannula 60 may include a dedicated wire lumen to protect and enclose the wires.

The device 200 includes a stylet 66 that may be movably inserted within the cannula 60 to urge the outermost clip from the device 200 when that clip engages tissue to be closed, with the removal of the outermost clip 70 aligning the next clip 70 for action upon neighboring tissue and removal with repeated operation of the arms 220, 230 via the operator 92.

In use, the hemostasis clip applicator device 10 (or device 200) may be loaded with one or a plurality of clips 70 (normally two or three) by threading the pins 78 extending from each of the first and second fingers 72, 73 of the clip 70 into a track 28 defined in the respective first and second arm 20, 30 of the device 10 (or first and second arm 220, 230 of the device 200). Other than the location of the position of the pivot point 40 of the first and second arms of the devices 10 and 200 and the different connection point between the wires and the first and second arms in the devices 10 and 200 (resulting in potentially different operation of the wires 82, 84 and operator 92 for the different embodiments), the device 10 and device 200 are generally constructed and operate in the same way. Accordingly, the operation and use of either device is consistent with the description of the device 10 here, with any exceptions for device 200 specifically noted here.

Clips 70 are installed between the first and second arms 20, 30 of device 10 in series such that the proximal end of the outer-most clip 70 contacts or is proximate to the distal end of the neighboring clip 70. After the clips 70 are inserted into the device 10, the device 10 is inserted into position within a patient (e.g. the GI tract) by being threaded through the working lumen of a previously positioned endoscope. The device 10 is urged into position by pushing the cannula 60 which similarly moves the first and second arms 20, 30 and the clips 70 disposed therebetween. While the device 10 is being positioned within the endoscope and patient, the operator 92 is maintained in the normal position, to avoid the first and second arms 20, 30 from pivoting with respect to each other, which would block further motion within the endoscope, and potentially damage the device 10, the endoscope or damage the patient's tissue, further complicating the procedure. In some embodiments, the cannula 60 may include markings upon the outer surface corresponding to the length of the cannula 60 inserted into the endoscope.

When the device 10 is fully inserted into the patient, the first and second arms 20, 30 are positioned outside of the endoscope lumen by urging the cannula 60 further within the endoscope, to allow the first and second arms 20, 30 to be outwardly pivoted, as well as to provide a view of the device 10 and the patient's tissue surrounding the endoscope by way of the camera or other remote vision system provided with the endoscope. The device 10 and the endoscope are then manipulated by the physician to align the distal ends 22, 32 of the first and second arms 20, 30 with the tissue (T, S, R, FIGS. 8-9) to be closed with the hemostatic clips 70.

When properly positioned, the physician moves the operator 92 disposed upon the handle 90 to pivot the first and second arms 20, 30 away from each other and similarly open the clips 70 disposed therebetween the same distance, which allows the tissue (T, S, R) to be positioned within the space between the jaws 74, 75 upon the clip 70 (as shown in FIG. 8). The operator 92 is then released, allowing the jaws 74, 75 to engage the selected tissue (T, S, R) therebetween due to the inward biasing force of the clips 70 (i.e. the outermost clip engaging the tissue and any clips 70 positioned within the device 10). Upon the clip closing and the jaws 74, 75 engaging the patient's tissue (T, S, R) the clip 70 is released from between the first and second arms 20, 30 by slowly withdrawing the cannula 60 from the endoscope, while maintaining the stylet 66 fixed. The relative motion between cannula 60 and stylet 66 causes the distal end 67 of the stylet 66 to advance within the arms 20, 30 and push the proximal end of the proximal most clip 70 between the arms 20, 30. The proximal most clip 70 accordingly pushes its neighboring clip 70, until the distal most clip 70 is slid through the track 28 and out of the device 10. The relative motion of the stylet 66 and cannula 60 is maintained for approximately the length of the clip 70, as monitored by a plurality of length markings 69 provided upon the stylet 66 (or cannula 60) and/or by viewing the device 10 and clip 70 through the endoscope's camera, or by a remote indication means such as ultrasound, x-ray, fluoroscopy and the like. When the clip 70 is released from the device 10, the device 10 may be repositioned to allow the next clip 70 between the first and second arms 20, 30 to engage further tissue to be closed by the clips 70. Alternatively, if the procedure is complete (or the all clips within the device have been released), the device 10 is removed from the patient by withdrawing both the cannula 60 and stylet 66 from the endoscope. The device 10 may be loaded with further clips 70 as necessary to continue the procedure, and the device 10 reinserted within the patient through the endoscope.

While the preferred embodiments of the disclosure have been described, it should be understood that the disclosure is not so limited and modifications may be made without departing from the disclosure. The scope of the invention is defined by the appended claims, and all devices that come within the meaning of the claims, either literally or by equivalence, are intended to be embraced therein.

What is claimed is:

1. A medical device comprising:
   first and second elongate arms, each arm comprising a distal end portion and a proximal end portion, the arms being pivotably connected about a connection located on each arm and forming a pivot point to allow relative motion between the first and second arms, the distal end portion of each of the first and second arms further comprising a track blindly defined from a distal end of each arm toward the proximal end portion of each arm, the distal end portions opposing eachother;

a clip slidably disposed between the opposed distal end portions of the first and second arms, the clip comprising first and second fingers each with distal and proximal portions, the proximal portions of the first and second fingers being fixed together to bias the distal portions of the first and second fingers toward each other to a closed position, the first and second fingers each further comprising a pin extending radially outward from the distal portion thereof and extending from a side of the respective first or second finger opposite to a clamping surface thereof;

wherein the pin from the first finger is slidably received within the track of the first arm, and the pin from the second finger is slidably received within the track of the second arm, wherein the first finger is associated with the first arm and the second finger is associated with the second arm, such that relative motion of the first and second arms away from each other urges similar relative motion of the first and second fingers away from each other.

2. The medical device of claim 1, wherein the first and second arms are pivotably connected together with a scissor-like connection, with the distal end portion and the proximal end portion of each arm disposed on opposite sides of the pivot connection.

3. The medical device of claim 2, wherein the proximal end portion of each arm is connected to a respective wire such that external forces applied to the proximal end portion of each arm by the wire urges the proximal end portions of the first and second arms away from each other.

4. The medical device of claim 2, further comprising a cannula disposed between the proximal end portions of the first and second arms and disposed behind the pivoting scissor-like connection, and an elongate member disposed through the cannula and configured to allow selective contact and application of longitudinal force to a rearmost clip disposed between the first and second arms.

5. The medical device of claim 4, wherein the elongate member can be remotely urged toward the distal end portions of the first and second arms to remove a distal-most clip from between the first and second arms.

6. The medical device of claim 2, further comprising an elongate member disposed between the first and second arms having a distal end portion that contacts the proximal end portions of the first and second fingers of a rearmost clip disposed within the device.

7. The medical device of claim 1, wherein the first and second arms are pivotably connected together at a proximal end thereof such that a force applied to the respective arm just distal of the pivoting connection causes like motion of the distal end of the respective arm.

8. The medical device of claim 1, wherein first and second arms comprise a relatively semi-circular outer profile, such that a cross-section of the first and second arms is substantially circular when pivoted together.

9. The medical device of claim 1, wherein the first and second arms are configured to receive one or more additional clips therebetween.

10. The medical device of claim 9, wherein the one or more additional clips are capable of being disposed with a distal portion of a first outermost clip of said one or more additional clips proximate the distal end portion of each of the first and second arms, and with a distal portion of a second clip of said one or more additional clips proximate a proximal portion of the first outermost clip of said one or more additional clips.

11. The medical device of claim 10, wherein the track of each arm is configured to receive pins from each of the one or more additional clips when the pins of the one or more additional clips are disposed therein.

12. The medical device of claim 1, wherein each pin extends substantially perpendicular to an outer surface of its respective finger.

13. The medical device of claim 1, wherein the first and second fingers are formed monolithically with each other.

14. The medical device of claim 1, wherein the first and second fingers are biased to the closed position with a torsion spring.

15. The medical device of claim 1, wherein the distal portions of each of the first and second fingers comprise an engagement portion configured to apply a sealing force to tissue disposed between the engagement portions when the medical device is used to clamp tissue.

16. The medical device of claim 15, wherein each of the engagement portions comprises one or more downwardly extending teeth and one or more upwardly extending recesses, wherein the engagement portions are aligned such that the one or more extending teeth of one of the engagement portions are in registry with the one or more recesses of the other of the engagement portions when the clip is in the closed position.

17. The medical device of claim 15, wherein the engagement portions are separated from each other when the first and second arms are pivotably separated from each other.

18. The medical device of claim 1, wherein each track is defined through an entire wall thickness of its respective arm.

19. The medical device of claim 1, wherein each track extends through only a portion of a wall thickness of its respective arm.

20. The medical device of claim 1, wherein each pin is a key and each track is a keyway.

21. The medical device of claim 1, wherein the first and second fingers are configured to urge the first and second arms toward each other when a force urging relative motion of the first and second arms away from each other is released.

22. The medical device of claim 21, wherein the first arm urges motion of the first finger and the second arm urges motion of the second finger based upon an engagement of the pin of the first and second finger within its respective track of the respective first and second arm.

23. The medical device of claim 1, wherein the first arm urges motion of the first finger and the second arm urges motion of the second finger based upon an engagement of the pin of the first and second finger within its respective track of the respective first and second arm.

24. A medical device comprising:

first and second elongate arms, each arm comprising a distal end portion and a proximal end portion, the arms being pivotably connected about a connection located on each arm and forming a pivot point to allow selective pivoting between a first closed position where the first and second arms are disposed substantially parallel to each other and a second open position where the first and second arms are disposed at oblique angles with respect to each other, the distal end portion of each of the first and second arms further comprising a track blindly defined from a distal end of each arm toward the proximal end portion of each arm, the distal end portions opposing eachother;

a clip slidably disposed between the opposed distal end portions of each of the first and second arms, the clip comprising first and second fingers each with distal and proximal portions, the first and second fingers each further comprising a pin extending radially outward from the distal portion thereof and extending from a side of the respective first or second finger opposite to a clamping surface thereof;

wherein the pin from the first finger is slidably received within the track of the first arm, and the pin from the second finger is slidably received within the track of the second arm, wherein the proximal portions of the first and second fingers are fixed together to bias the distal portions of the first and second fingers toward each other to a closed position such that the first and second arms are biased to the closed position when the pins from the respective fingers are engaged with the tracks on the respective arms, wherein the first finger is associated with the first arm and the second finger is associated with the second arm, such that relative motion of the first and second arms away from each other urges similar relative motion of the first and second fingers away from each other.

25. The medical device of claim 24, wherein the first and second fingers are configured to urge the first and second arms toward each other when a force urging relative motion of the first and second arms away from each other is released.

26. The medical device of claim 25, wherein the first arm urges motion of the first finger and the second arm urges motion of the second finger based upon an engagement of the pin of the first and second finger within its respective track of the respective first and second arm.

27. The medical device of claim 24, wherein the first arm urges motion of the first finger and the second arm urges motion of the second finger based upon the engagement of the pin of the respective first and second finger within the track of the respective first and second arm.

\* \* \* \* \*